(12) United States Patent
Pettit

(10) Patent No.: US 8,202,264 B1
(45) Date of Patent: Jun. 19, 2012

(54) BOWEL MOVEMENT PAD SYSTEM

(76) Inventor: Lori L. Pettit, Safety Harbor, FL (US)

( * ) Notice: Subject to any disclaimer, the term of this patent is extended or adjusted under 35 U.S.C. 154(b) by 261 days.

(21) Appl. No.: 12/655,774

(22) Filed: Jan. 7, 2010

(51) Int. Cl.
*A61F 13/15* (2006.01)
*A41B 9/02* (2006.01)

(52) U.S. Cl. ........ 604/396; 604/394; 604/397; 604/387; 604/385.14; 604/385.03; 604/385.13; 2/403; 2/404; 2/405

(58) Field of Classification Search .................. 604/396, 604/394, 397, 387, 385.14, 385.03, 385.13; 2/403, 404, 405
See application file for complete search history.

(56) References Cited

U.S. PATENT DOCUMENTS

| 5,405,342 | A | 4/1995 | Roessler |
| 6,502,695 | B1* | 1/2003 | Kim et al. .................... 206/440 |
| 6,623,466 | B1 | 9/2003 | Richardson |
| 7,341,580 | B2 | 3/2008 | Hamilton-Vance |

\* cited by examiner

*Primary Examiner* — Jacqueline F. Stephens

(57) ABSTRACT

A pad in a generally T-shaped configuration has a central section with a height and a cross section with a width. The central section has generally parallel edges remote from the cross section. The pad has an exterior surface and also an interior surface positionable in facing contact with the interior surface of pants. A central adhesive strip in a rectangular configuration extends for between 40 percent and 60 percent of its length along the length of the central section. The central adhesive strip extends for between 40 percent and 60 percent of its length through the cross section. Each of two laterally disposed side adhesive strips is in a rectangular configuration with a width essentially equal to the width of the central adhesive strip and a length extending for between 30 percent and 40 percent of its length of the central adhesive strip.

1 Claim, 3 Drawing Sheets

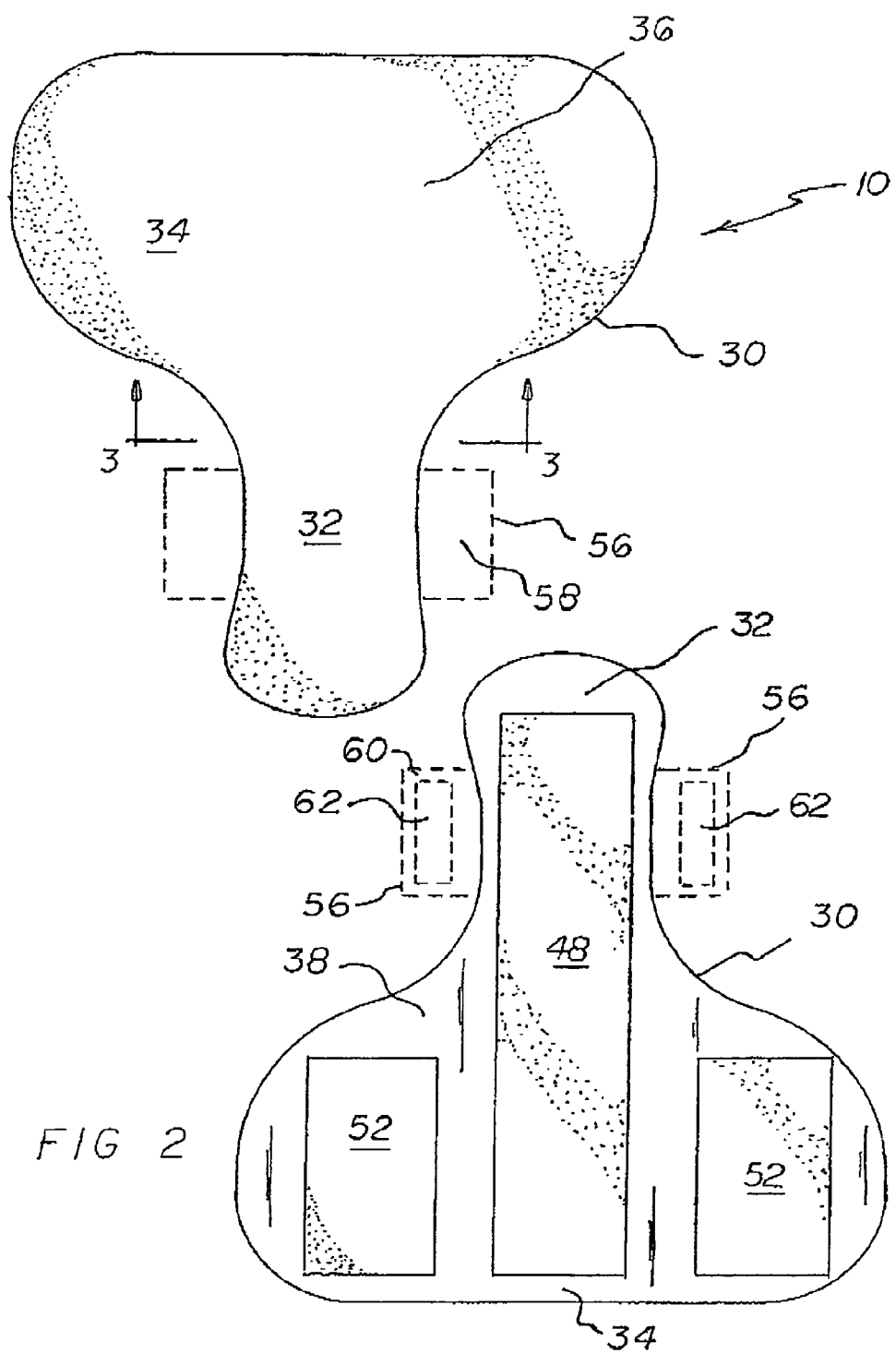

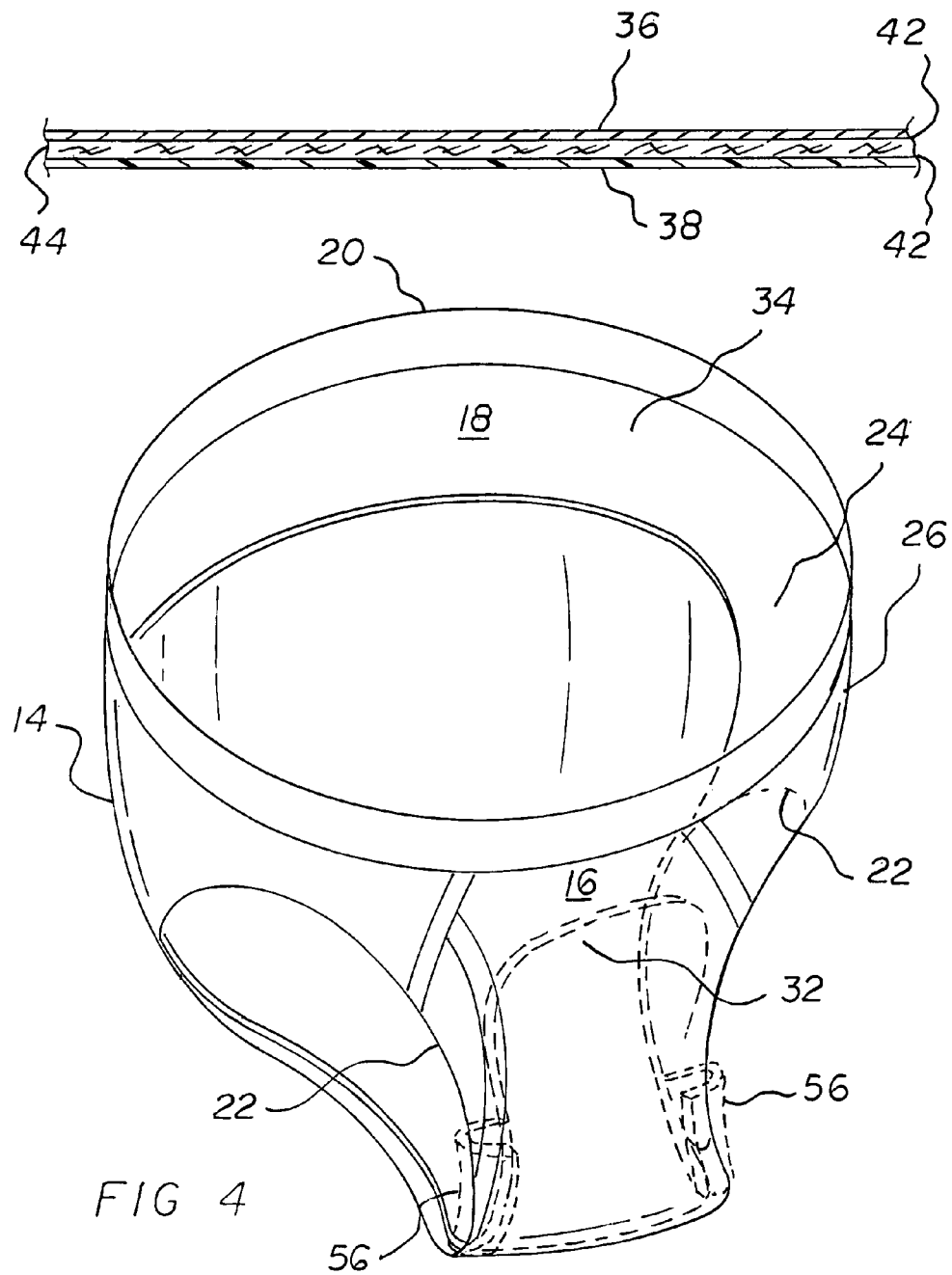

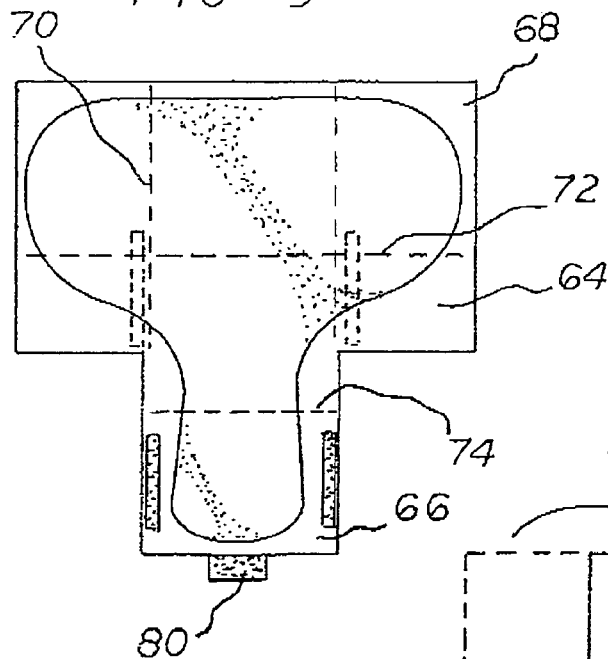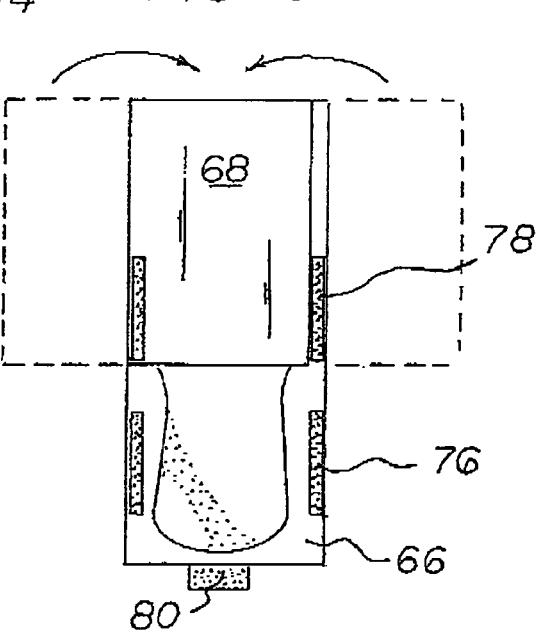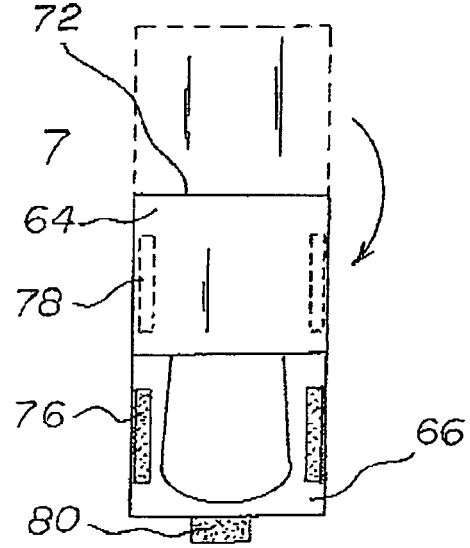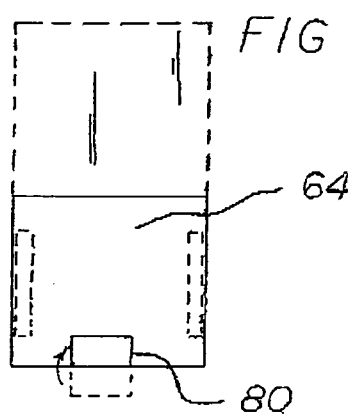

BOWEL MOVEMENT PAD SYSTEM

BACKGROUND OF THE INVENTION

1. Field of the Invention

The present invention relates to a bowel movement pad system and more particularly pertains to absorbing excrement of a child without soiling garments, the absorbing being done in a sanitary, safe, convenient and economical manner.

2. Description of the Prior Art

The use of liner and pad systems for a child's underpants of known designs and configurations is known in the prior art. More specifically, liner and pad systems for a child's underpants of known designs and configurations previously devised and utilized for the purpose of absorbing excrement while avoiding soiling garments are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 7,341,580 issued Mar. 11, 2008 to Hamilton-Vance relates to a Protective Liner and a Method for Using a Protective Liner. U.S. Pat. No. 6,623,466 issued Sep. 23, 2003 to Richardson relates to an Absorbent Article Having Detachable Components. Lastly, U.S. Pat. No. 5,405,342 issued Apr. 11, 1995 to Roessler relates to a Disposable Absorbent Article with Flushable Insert.

While these devices fulfill their respective, particular objectives and requirements, the aforementioned patents do not describe a bowel movement pad system that allows absorbing excrement of a child without soiling garments, the absorbing being done in a sanitary, safe, convenient and economical manner.

In this respect, the bowel movement pad system according to the present invention substantially departs from the conventional concepts and designs of the prior art, and in doing so provides an apparatus primarily developed for the purpose of absorbing excrement of a child without soiling garments, the absorbing being done in a sanitary, safe, convenient and economical manner.

Therefore, it can be appreciated that there exists a continuing need for a new and improved bowel movement pad system which can be used for absorbing excrement of a child without soiling garments, the absorbing being done in a sanitary, safe, convenient and economical manner. In this regard, the present invention substantially fulfills this need.

SUMMARY OF THE INVENTION

In view of the foregoing disadvantages inherent in the known types of liner and pad systems for a child's underpants of known designs and configurations now present in the prior art, the present invention provides an improved bowel movement pad system. As such, the general purpose of the present invention, which will be described subsequently in greater detail, is to provide a new and improved bowel movement pad system and method which has all the advantages of the prior art and none of the disadvantages.

To attain this, the present invention essentially comprises jockey shorts having a fly front and an imperforate back. The shorts have a waist opening with a primary edge above. The shorts also have laterally disposed leg openings each with a secondary edge below. The shorts have an interior surface and an exterior surface.

Next, a pad is provided. The pad is in a generally T-shaped configuration. The pad has a central section with a height of between 8 inches and 9 inches. The pad has a cross section with a width of between 7.5 inches and 8.5 inches. The central section has generally parallel edges remote from the cross section with a width of between 1.5 inches and 2.5 inches. The pad has an exterior surface. The pad also has an interior surface positionable in facing contact with the interior surface of the jockey shorts.

The pad is fabricated of two exterior layers comprised of a liquid pervious top sheet to maintain the child's skin relatively dry, a liquid impervious back sheet to maintain the pad in contact with the jockey shorts, and the pad also being fabricated of a central layer of a hydrophilic material to absorb and retain excrement.

Next, a central adhesive strip in a rectangular configuration is provided. The central adhesive strip extends for between 40 percent and 60 percent of its length along the length of the central section. The central adhesive strip extends for between 40 percent and 60 percent of its length through the cross section.

Also provided are two laterally disposed side adhesive strips. Each of the side adhesive strips is in a rectangular configuration with a width equal to the width of the central adhesive strip and a length extending for between 30 percent and 40 percent of the length of the central adhesive strip.

The central section of the pad and a portion of the central adhesive strip are adhesively secured to the interior surface of the jockey shorts and extend from adjacent to the waistband downwardly between the leg openings. The cross section of the pad and a portion of the central adhesive strip and the entirety of the side adhesive strips are adhesively secured to the interior surface of the jockey shorts and extend upwardly along the back of the jockey shorts toward the waistband.

Next provided are two similarly configured supplemental wings. Each supplemental wing is in a rectangular configuration and extends laterally outwardly from the central section of the pad. The wings have an exterior surface and an interior surface. An adhesive patch is provided on the interior surface of each wing. The wings are folded around the secondary edge of each leg opening and adhesively secured to the exterior surface of the jockey shorts.

Lastly, a foldable cover is provided. The foldable cover is fabricated of a moisture impervious material. The cover has a rectangular central region and a rectangular cross region. The cover is of a size to receive the pad after the pad has been soiled. The cover has vertical fold lines as extensions of the central region. The cover has an upper horizontal fold line at an upper third of the cover and a lower horizontal fold line at a lower third of the cover. Vertically extending adhesive strips are provided on the central region. Vertically extending adhesive strips are provided on the cross region. The vertically extending adhesive strips function to secure the pad within the cover after folding. A horizontal adhesive strip depends downwardly from the central region and is adapted to be folded into contact with the cross region after the cover has been folded to conceal the pad therein.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved bowel movement pad system which has all of the advantages of the prior art liner and pad systems for a child's underpants of known designs and configurations and none of the disadvantages.

It is another object of the present invention to provide a new and improved bowel movement pad system which may be easily and efficiently manufactured and marketed.

It is further object of the present invention to provide a new and improved bowel movement pad system which is of durable and reliable constructions.

An even further object of the present invention is to provide a new and improved bowel movement pad system which is susceptible of a low cost of manufacture with regard to both materials and labor, and which accordingly is then susceptible of low prices of sale to the consuming public, thereby making such bowel movement pad system economically available to the buying public.

Even still another object of the present invention is to provide a bowel movement pad system for absorbing excrement of a child without soiling garments, the absorbing being done in a sanitary, safe, convenient and economical manner.

Lastly, it is an object of the present invention to provide a new and improved bowel movement pad system having a pad in a generally T-shaped configuration with a central section with a height and a cross section with a width. The central section has generally parallel edges remote from the cross section. The pad has an exterior surface and also an interior surface positionable in facing contact with the interior surface of pants. A central adhesive strip in a rectangular configuration extends for between 40 percent and 60 percent of its length along the length of the central section. The central adhesive strip extends for between 40 percent and 60 percent of its length through the cross section. Each of two laterally disposed side adhesive strips is in a rectangular configuration with a width essentially equal to the width of the central adhesive strip and a length extending for between 30 percent and 40 percent of its length of the central adhesive strip.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of a bowel movement pad system constructed in accordance with the principles of the present invention.

FIG. 2 is a rear elevational view of the system shown in FIG. 1.

FIG. 3 is a cross sectional view taken along line 3-3 of FIG. 1.

FIG. 4 is a perspective illustration of a bowel movement pad operatively coupled to jockey shorts for use in system configuration.

FIGS. 5 through 8 show a wrapper for encompassing a soiled bowel movement pad to facilitate disposal.

The same reference numerals refer to the same parts throughout the various Figures.

DESCRIPTION OF THE PREFERRED EMBODIMENT

With reference now to the drawings, and in particular to FIG. 1 thereof, the preferred embodiment of the new and improved bowel movement pad system embodying the principles and concepts of the present invention and generally designated by the reference numeral 10 will be described.

The present invention, the bowel movement pad system 10 is comprised of a plurality of components. Such components in their broadest context include a pad, a central adhesive strip, and two laterally disposed side adhesive strips. Such components are individually configured and correlated with respect to each other so as to attain the desired objective.

First provided are jockey shorts 14. The jockey shorts have a fly front 16 and an imperforate back 18. The jockey shorts have a waist opening with a primary edge 20 above. The jockey shorts also have laterally disposed leg openings each with a secondary edge 22 below. The jockey shorts have an interior surface 24 and an exterior surface 26.

Next, a pad 30 is provided. The pad is in a generally T-shaped configuration. The pad has a central section 32 with a height of between 8 inches and 9 inches. The pad has a cross section 34 with a width of between 7.5 inches and 8.5 inches. The central section has generally parallel edges remote from the cross section with a width of between 1.5 inches and 2.5 inches. The pad has an exterior surface 36. The pad also has an interior surface 38 positionable in facing contact with the interior surface of the jockey shorts.

The pad is fabricated of two exterior layers 42 comprised of a liquid pervious top sheet to maintain the child's skin relatively dry, a liquid impervious back sheet to maintain the pad in contact with the jockey shorts, and the pad also being fabricated of a central layer 44 of a hydrophilic material to absorb and retain excrement.

Next, a central adhesive strip 48 in a rectangular configuration is provided. The central adhesive strip extends for between 40 percent and 60 percent of its length along the length of the central section. The central adhesive strip extends for between 40 percent and 60 percent of its length through the cross section.

Also provided are two laterally disposed side adhesive strips 52. Each of the side adhesive strips is in a rectangular configuration with a width equal to the width of the central adhesive strip and a length extending for between 30 percent and 40 percent of the length of the central adhesive strip.

The central section of the pad and a portion of the central adhesive strip are adhesively secured to the interior surface of the jockey shorts and extend from adjacent to the waistband downwardly between the leg openings. The cross section of the pad and a portion of the central adhesive strip and the entirety of the side adhesive strips are adhesively secured to the interior surface of the jockey shorts and extend upwardly along the back of the jockey shorts toward the waistband.

Next provided are two similarly configured supplemental wings 56. Each supplemental wing is in a rectangular configuration and extends laterally outwardly from the central section of the pad. The wings have an exterior surface 58 and an interior surface 60. An adhesive patch 62 is provided on the interior surface of each wing. The wings are folded around the secondary edge of each leg opening and adhesively secured to the exterior surface of the jockey shorts.

Lastly, a foldable cover 64 is provided. The foldable cover is fabricated of a moisture impervious material. The cover has a rectangular central region 66 and a rectangular cross region 68. The cover is of a size to receive the pad after the pad has been soiled. The cover has vertical fold lines 70 as extensions of the central region. The cover has an upper horizontal fold line 72 at an upper third of the cover and a lower horizontal fold line 74 at a lower third of the cover. Vertically extending adhesive strips 76 are provided on the central region. Vertically extending adhesive strips are provided on the cross region 78. The vertically extending adhesive strips function to secure the pad within the cover after folding. A horizontal adhesive strip 80 depends downwardly from the central region and is adapted to be folded into contact with the cross region after the cover has been folded to conceal the pad therein.

The present invention is a thin pad which is selectively placed and removable within underwear. The thin pad provides a protective barrier between the child's skin and the underwear. When a bowel movement occurs, the bottom layer of the pad will prevent the stool and any leakages from getting on the child's underwear, clothing or other surfaces. The middle layer will absorb any liquid stool from the bowel movement, i.e. in cases of diarrhea or fecal soiling. The soft top layer provides comfort while wearing. The large seat area is needed to provide underwear coverage if the stool spreads. The narrow crotch area is needed to provide underwear coverage if the stool spreads into this area. The thickness of this pad is similar to the thickness of an ultra thin feminine napkin or pantiliner. The wings feature aids in keeping the pad securely in place in the underwear. The present invention assists a parent or caregiver of a child in potty training of the child and aids in progressing a child into underwear. The present invention removes the temptation of a child who is potty trained for urine but not stool to continue to use pull-on diapers rather than transition to underwear.

The present invention is quick and easy to change. There is less mess to be cleaned. It is more sanitary. It is disposable and there is less disposable waste as compared to diapers or pull-on diapers. The present invention eliminates fecal soiling or liquid stool in underwear. It eliminates stains in underwear. It eliminates leakage onto pants/shorts or other surfaces where the child might play. It helps protect other children from coming into contact with stool leakages. It eliminates having to pre-wash and pre-soak underwear and reduces the times that underwear must be washed. The present invention helps to eliminate some of the potty training frustration and stress experienced by the parent or caregiver and the child.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A bowel movement pad system for absorbing excrement of a child without soiling worn garments, the system comprising, in combination:

jockey shorts having a fly front, an imperforate back, a waist opening with a primary edge above and laterally disposed leg openings each with a secondary edge below, the jockey shorts having an interior surface and an exterior surface;

a pad in a generally T-shaped configuration with a central section with a height of between 8 inches and 9 inches and a cross section with a width of between 7.5 inches and 8.5 inches, the central section having generally parallel edges remote from the cross section with a width of between 1.5 inches and 2.5 inches, the pad having an exterior surface and an interior surface positionable in facing contact with the interior surface of the jockey shorts;

the pad being fabricated of two exterior layers comprised of a liquid pervious top sheet to maintain the child's skin relatively dry, a liquid impervious back sheet to maintain the pad in contact with the jockey shorts, and the pad also being fabricated of a central layer of a hydrophilic material to absorb and retain excrement;

a central adhesive strip in a rectangular configuration extending for between 40 percent and 60 percent of its length along the length of the central section, the central adhesive strip extending for between 40 percent and 60 percent of its length through the cross section;

two laterally disposed side adhesive strips, each in a rectangular configuration with a width equal to the width of the central adhesive strip and a length extending for between 30 percent and 40 percent of the length of the central adhesive strip;

the central section of the pad and a portion of the central adhesive strip adhesively secured to the interior surface of the jockey shorts and extending from adjacent to the waistband downwardly between the leg openings, the cross section of the pad and a portion of the central adhesive strip and the entirety of the side adhesive strips adhesively secured to the interior surface of the jockey shorts and extending upwardly along the back of the jockey shorts toward the waistband;

two similarly configured supplemental wings, each supplemental wing being in a rectangular configuration extending laterally outwardly from the central section of the pad, the wings having an exterior surface and an interior surface with a supplemental adhesive patch on the interior surface of each wing, the supplemental adhesive patches being spaced from the central adhesive strip and the side adhesive strips, the wings being folded around the secondary edge of each leg opening and adhesively secured to the exterior surface of the jockey shorts; and a foldable cover fabricated of a moisture impervious material, the cover having a rectangular central region and a rectangular cross region, the cover being of a size to receive the pad after the pad has been soiled, the cover having vertical fold lines as extensions of the central region, the cover having an upper horizontal fold line at an upper third of the cover and a lower horizontal fold line at a lower third of the cover, vertically extending adhesive strips on the central region and vertically extending adhesive strips on the cross region for securing the pad within the cover after folding, the vertically extending adhesive strips on the central region being spaced from the vertically extending adhesive strips on the cross region, and a horizontal strip depending downwardly from the central region and adapted to be folded into contact with the cross region after the cover has been folded to conceal the pad therein.

* * * * *